(12) United States Patent
Fang et al.

(10) Patent No.: US 8,039,234 B1
(45) Date of Patent: Oct. 18, 2011

(54) METHODS, PANELS OF IDENTIFICATION MARKERS, AND KITS FOR IDENTIFYING FORENSIC SAMPLES

(75) Inventors: Rixun N. Fang, Palo Alto, CA (US); Manohar R. Furtado, San Ramon, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 552 days.

(21) Appl. No.: 11/751,845

(22) Filed: May 22, 2007

Related U.S. Application Data

(60) Provisional application No. 60/747,927, filed on May 22, 2006.

(51) Int. Cl.
*C07H 21/04* (2006.01)
*C12P 19/34* (2006.01)

(52) U.S. Cl. ......... 435/91.1; 435/6; 435/91.2; 536/24.3; 536/24.32

(58) Field of Classification Search .................. None
See application file for complete search history.

(56) References Cited

U.S. PATENT DOCUMENTS 5,334,499 A * 8/1994 Burdick et al. .............. 435/6
7,582,435 B2   9/2009 Ballantyne et al.

OTHER PUBLICATIONS

Affymetrix GeneChip Human Genome U133 Set (2001), plus supporting print copies, eighteen pages total.*
Jusola et al. Forensic Science International 152 (2005) 1-12.*
New England Biolabs Catalog (1998/1999), pp. 121, 284.*
Rothstein et al. (1994) PNAS USA 91: 4155-4159.*
Fang et al. International Congress Series 1288 (2006) 685-687.*
Bauer, Martin , "Evaluation of mRNA Markers for the Identification of Menstrual Blood", *J Forensic Sci* vol. 47, No. 6 Nov. 2002 , 1-5.
Fang, R. et al., "Real-time PCR assays for the detection of tissue and body fluid specific mRNAs", *International Congress Series* vol. 1288 pp. 685-687 2005.
Fleming, Rachel et al., "The development of a mRNA multiplex RT-PCR assay for the definitive identification of body fluids", *Forensic Science International: Genetics* 2009 , 1-13.
Haas, C. et al., "mRNA profiling for body fluid identification", *Forensic Science International: Genetics Supplement Series 1* 2008 , 37-38.
Juusola, Jane et al., "Messenger RNA profiling: a prototype method to supplant conventional methods for body fluid identification", *Forensic Science International* 135 2003 , 85-96.
Juusola, Jane et al., "mRNA Profiling for Body Fluid Identification by Multiplex Quantitative RT-PCR", *J Forensic Sci* vol. 52, No. 6 Nov. 2007 , 1252-1262.

\* cited by examiner

*Primary Examiner* — Juliet Switzer
(74) *Attorney, Agent, or Firm* — John W. Burns; Shirley A. Recipon

(57) ABSTRACT

Methods for identifying forensic samples using panels of markers and gene expression profiling, including without limitation, mRNA profiling, miRNA profiling, or both, are disclosed. Panels of markers for identifying certain tissue samples and certain body fluid samples are also disclosed. Kits for expediting performance of certain of the disclosed methods are provided.

19 Claims, 1 Drawing Sheet

Figure 1:
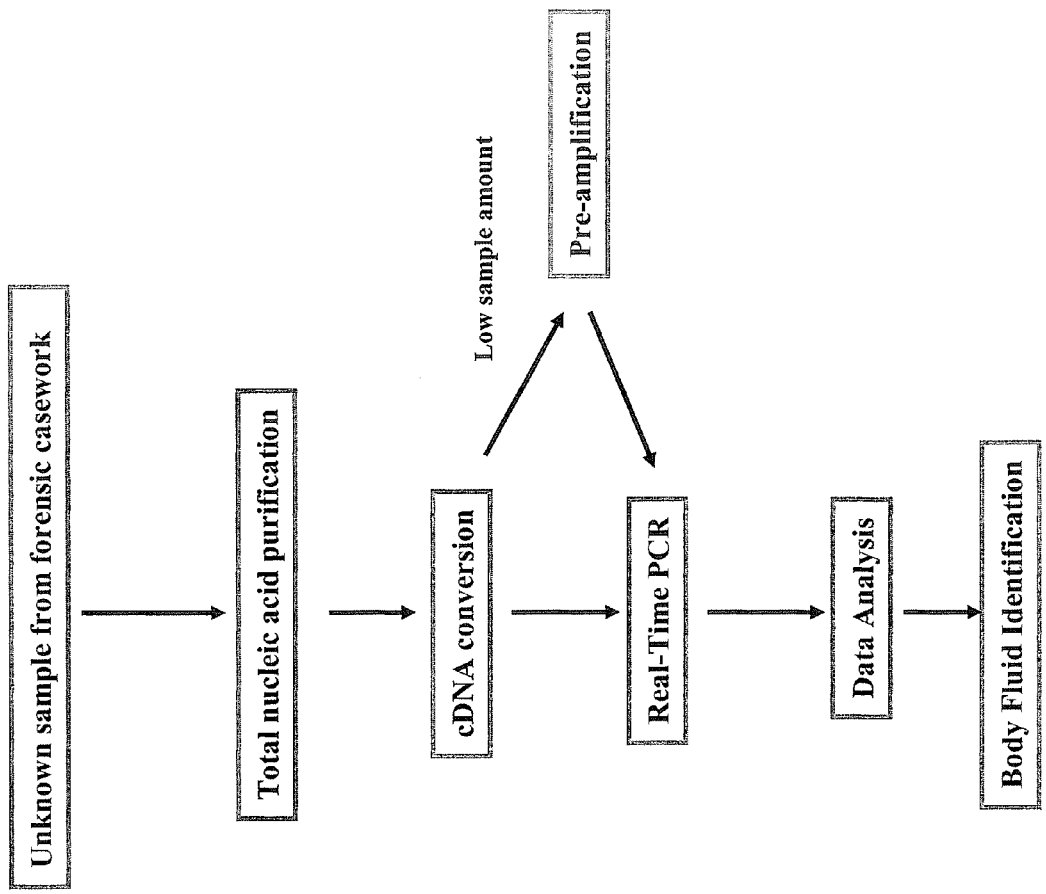

METHODS, PANELS OF IDENTIFICATION MARKERS, AND KITS FOR IDENTIFYING FORENSIC SAMPLES

CROSS-REFERENCE TO RELATED APPLICATIONS

This application claims a priority benefit under 35 U.S.C. §119(e) from U.S. Application No. 60/747,927, filed May 22, 2006, the contents of which are incorporated herein by reference.

FIELD

Methods, panels of markers for generating gene expression profiles, and kits for identifying a forensic sample are provided.

INTRODUCTION

Body fluids and stains are frequently encountered at crime scenes, including but not limited to, blood, semen, saliva, and vaginal secretions. Traditional methods for identifying body fluids are often labor-intensive, time-consuming, and expensive. There is a need for more efficient, less expensive body fluid identification techniques. The identification of tissue samples is also important to forensic scientists.

Advances in gene expression analysis have allowed scientists to gain a better understanding of, among other things, developmental biology and carcinogenesis. Expression profiles have identified highly expressed genes based on cell and/or tissue type. However, these techniques typically require relatively large amounts of messenger RNA (mRNA) or microRNA (miRNA) to obtain reliable results. Forensic samples are often small and the quantity of nucleic acid obtained from such samples is correspondingly low. If appropriate quantities of nucleic acid could be obtained from typical crime scene samples, gene expression analysis could be employed by forensic scientists for determining the source of such samples, particularly if panels of suitable body fluid-specific markers and tissue-specific markers were available to facilitate identification.

SUMMARY

The present teachings are directed to methods, marker panels, and kits for identifying a forensic sample by determining the relative concentration of the RNA species that correspond to a panel of markers comprising genes that are differentially expressed in various samples, including mRNA markers, miRNA markers, or both. The methods permit the identification of forensic samples, including without limitation, tissue or organ samples (collectively referred to in this specification as a "tissue sample") or body fluid samples using certain tissue marker panels and body fluid marker panels of the current teachings. According to certain disclosed methods, nucleic acid is obtained from a sample and a gene expression profile for the markers in the panel is generated, typically using a marker-specific primer pair for each marker. By comparing the gene expression profile generated from the sample with the known expression profile of those markers in certain tissue samples and body fluids, the sample can generally be identified. According to certain methods, a reverse transcriptase or a DNA-dependent DNA polymerase with reverse transcriptase activity, for example but not limited to, Tth DNA polymerase is bined with a gene-specific first primer for each target to be analyzed and a DNA complement of the RNA target is generated. This is followed by PCR amplification using a gene-specific primer pair or a gene-specific primer and a universal primer for each marker. Certain of the disclosed methods employ two PCR amplification reactions, including without limitation, a first PCR reaction that is performed for a limited cycle multiplex reaction followed by a second amplification reaction, often performed as a single-plex reaction (see, e.g., U.S. Pat. No. 6,605,451 (Marmaro and Gerdes); U.S. Patent Application Publication No. 2004/0175733 A1 (Andersen and Ruff); and Dolganov et al., Genome Research 11:1473-83, 2001). Certain embodiments of the disclosed methods include multiplex assays for quantitating a multiplicity of different small RNA species; other embodiments are directed to single-plex assays for detecting or quantitating a single small RNA species, including without limitation a series of two or more single-plex assays performed in parallel. Typically the multiplicity of different RNA species that are amplified and quantitated are members of a panel of markers, each of which is indicative of a particular tissue or body fluid. In certain embodiments, an internal standard, for example but not limited to a mRNA transcript of housekeeping gene, is also amplified and quantitated as a control.

In other embodiments, mRNA and/or miRNA profiling comprises a microarray, including but not limited to a planar array and a bead-based array, wherein the relative concentration of two different species of miRNA and/or mRNA are determined using well-known hybridization-based techniques and the sample is identified. In certain embodiments, a bead-based array comprises flow cytometry.

Kits for performing certain of the instant methods are also disclosed. Certain kit embodiments include at least one pair of primers for each of the markers in an identification panel, wherein each primer pair is designed to amplify one of the markers in the panel; appropriate nucleotide triphosphates (NTPs, including without limitation ribonucleotide triphosphates (rNTPs) and/or deoxyribonucleotide triphosphates (dNTPs), as appropriate); and a suitable polymerase. Certain kits comprise a RNA-dependent DNA polymerase and a DNA-dependent DNA polymerase. Some kits further comprise a reporter probe (sometimes referred to as a "non-priming oligonucleotide probe") for each marker amplicon; a nucleic acid dye; a miRNA linker probe (see U.S. Patent Application Pub. No. US 2005/0266418); an internal reference dye; a control sequence or internal standard; a reporter group, including without limitation an NTP comprising a reporter group; or combinations thereof. In certain embodiments, kits comprise a promoter-primer for each RNA sequence to be amplified, a polymerase, appropriate NTPs, a reporter group, including without limitation a NTP comprising a reporter group, or combinations thereof. In certain embodiments, kits comprise a microarray, a microfluidics device, a reaction vessel, or combinations thereof.

These and other features of the present teachings are set forth herein.

DRAWINGS

The skilled artisan will understand that the drawings, described below, are for illustration purposes only. These figures are not intended to limit the scope of the present teachings in any way.

FIG. 1: schematically depicts an illustrative workflow comprising certain aspects of various embodiments of exemplary methods of the current teachings.

DESCRIPTION OF EXEMPLARY EMBODIMENTS

It is to be understood that both the foregoing general description and the following detailed description are exemplary and explanatory only and are not intended to limit the scope of the current teachings. In this application, the use of the singular includes the plural unless specifically stated otherwise. For example, "a forward primer" means that more than one forward primer can be present, such as, one or more copies of a particular forward primer species, as well as one or more copies of different forward primer species. Also, the use of "comprise", "contain", and "include", or modifications of those root words, for example but not limited to, "comprises", "contained", and "including", are not intended to be limiting.

The section headings used herein are for organizational purposes only and are not to be construed as limiting the described subject matter in any way. All literature and similar materials cited in this application, including patents, patent applications, articles, books, and treatises are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "corresponding" as used herein refers to at least one specific relationship between the elements to which the term relates. For example, but without limitation, a particular marker-specific primer pair corresponds to the amplicon of that marker that the pair amplifies; and a forward primer of a given primer pair corresponds to the reverse primer of that primer pair.

The terms "DNA polymerase" and "polymerase" are used in a broad sense herein and refer to any polypeptide that catalyzes the addition of deoxyribonucleotides or analogs of deoxyribonucleotides to a nucleic acid polymer in a template dependent manner. For example but not limited to, the sequential addition of deoxyribonucleotides to the 3'-end of a primer that is annealed to a nucleic acid template during a primer extension reaction. Typically DNA polymerases include DNA-dependent DNA polymerases and RNA-dependent DNA polymerases, including without limitation, reverse transcriptases. Certain reverse transcriptases possess DNA-dependent DNA polymerase activity under certain reaction conditions, including AMV reverse transcriptase and MMLV reverse transcriptase. Such reverse transcriptases with DNA-dependent DNA polymerase activity may be suitable for use with the disclosed methods and are expressly within the contemplation of the current teachings. Descriptions of DNA polymerases can be found in, among other places, Lehninger Principles of Biochemistry, 3d ed., Nelson and Cox, Worth Publishing, New York, N.Y., 2000, particularly Chapters 26 and 29; Twyman, Advanced Molecular Biology: A Concise Reference, Bios Scientific Publishers, New York, N.Y., 1999; Ausubel et al., Current Protocols in Molecular Biology, John Wiley & Sons, Inc., including supplements through May 2006 (hereinafter "Ausubel et al."); Lin and Jaysena, J. Mol. Biol. 271:100-11, 1997; Pavlov et al., Trends in Biotechnol. 22:253-60, 2004; and Enzymatic Resource Guide: Polymerases, 1998, Promega, Madison, Wis. Expressly within the intended scope of the term DNA polymerase are enzymatically active mutants or variants thereof, including without limitation enzymes modified to confer different temperature-sensitive properties (see, e.g., U.S. Pat. Nos. 5,773,258; 5,677,152; and 6,183,998; and DNA Amplification: Current Techniques and Applications, Demidov and Broude, eds., Horizon Bioscience, 2004, particularly in Chapter 1.1) and enzymatically active fragments of certain DNA polymerases such as Klenow fragment and Stoffel fragment.

The term "nucleic acid dye" as used herein refers to a fluorescent molecule that is specific for a double-stranded polynucleotide or that at least emits a substantially greater fluorescent signal when associated with a double-stranded polynucleotide than with a single-stranded polynucleotide. Typically nucleic acid dye molecules associate with double-stranded segments of polynucleotides by intercalating between the base pairs of the double-stranded segment, by binding in the major or minor grooves of the double-stranded segment, or both. Non-limiting examples of nucleic acid dyes include ethidium bromide, DAPI, Hoechst derivatives including without limitation Hoechst 33258 and Hoechst 33342, intercalators comprising a lanthanide chelate (for example but not limited to a napthalene diimide derivative carrying two fluorescent tetradentate 3-diketone-Eu3+ chelates (NDI-(BHHCT-Eu$^{3+}$)$_2$), see, e.g., Nojima et al., Nucl. Acids Res. Supplement No. 1, 105-06 (2001)), ethidium bromide, and certain unsymmetrical cyanine dyes such as SYBR Green®, PicoGreen® (both available from Molecular Probes-Invitrogen), and BOXTO (TATAA Biocenter AB). An "unsymmetrical cyanine dye", sometimes described in the art as an asymmetric cyanine dye or an asymmetrical cyanine dye, refers to a dye molecule with the general formula $R_2N[CH=CH]_n CH=NR_2$, where n is a small number and the R groups typically comprise at least one benzazole group and at least one quinoline group or at least one pyridine group. Non-limiting examples of unsymmetrical cyanine dyes include [2-[N-(3-dimethylaminopropyl)-N-propylamino]-4-[2,3-dihydro-3-methyl-(benzo-1,3-thiazol-2-yl)-methylidene]-1-phenyl-quinolinium] (SYBR® Green), [2-[N-bis-(3-dimethylaminopropyl)-amino)-amino]-4-[2,3-dihydro-3-methyl-(benzo-1,3-thiazol-2-yl)-methylidene]-1-phenyl-quinolinium] (PicoGreen®), 4-[(3-methyl-6-(benzothiazol-2-yl)-2,3-dihydro-(benzo-1,3-thiazole)-2-methylidene)]-1-methyl-pyridinium iodide (BEBO), BOXTO, and BETO. Descriptions of unsymettrical cyanine dyes can be found in, among other places, Karlsson et al., Nucl. Acids Res. 31:6227-34 (2003); Zipper et al., Nucl. Acids Res. 32:e103 (2004); Bengtsson et al., Nucl. Acids Res. 31:e45 (2003); and Goransson et al., Asymettric cyanine dyes, DNA-Technology 2005, Chalmers University Technology (2005).

The term "reporter group" is used in a broad sense herein and refers to any identifiable tag, label, or moiety. The skilled artisan will appreciate that many different species of reporter groups can be used in the present teachings, either individually or in combination with one or more different reporter group. In certain embodiments, a reporter group emits a fluorescent, a chemiluminescent, a bioluminescent, a phosphorescent, or an electrochemiluminescent signal. Some non-limiting examples of reporter groups include fluorophores, radioisotopes, chromogens, enzymes, antigens including but not limited to epitope tags, semiconductor nanocrystals such as quantum dots, heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass spectrometer-compatible reporter groups, such as mass tags; charge tags, and isotopes (see, e.g., Haff and Smirnov, Nucl. Acids Res. 25:3749-50, 1997; Xu et al., Anal. Chem. 69:3595-3602; 1997; Sauer et al., Nucl. Acids Res. 31:e63, 2003).

The term reporter group also encompasses an element of multi-element reporter systems, including without limitation, affinity tags such as biotin:avidin, antibody:antigen, and the like, in which one element interacts with one or more other elements of the system in order to effect the potential for a detectable signal. Some non-limiting examples of multi-element reporter systems include an oligonucleotide comprising a biotin reporter group and a streptavidin-conjugated fluorophore, or vice versa; an oligonucleotide comprising a DNP reporter group and a fluorophore-labeled anti-DNP antibody; and the like. Detailed protocols for attaching reporter groups to nucleic acids can be found in, among other places, Hermanson, Bioconjugate Techniques, Academic Press, San Diego, 1996; Current Protocols in Nucleic Acid Chemistry, Beaucage et al., eds., John Wiley & Sons, New York, N.Y. (2000), including supplements through April 2005; and Haugland, Handbook of Fluorescent Probes and Research Products, $9^{th}$ ed., Molecular Probes, 2002.

Multi-element interacting reporter groups are also within the intended scope of the term reporter group, such as fluorophore-quencher pairs, including without limitation fluorescent quenchers and dark quenchers (also known as non-fluorescent quenchers). A fluorescent quencher can absorb the fluorescent signal emitted from a fluorophore and after absorbing enough fluorescent energy, the fluorescent quencher can emit fluorescence at a characteristic wavelength, e.g., fluorescent resonance energy transfer (FRET). For example without limitation, the FAM-TAMRA pair can be illuminated at 492 nm, the excitation peak for FAM, and emit fluorescence at 580 nm, the emission peak for TAMRA. A dark quencher, appropriately paired with a fluorescent reporter group, absorbs the fluorescent energy from the fluorophore, but does not itself fluoresce. Rather, the dark quencher dissipates the absorbed energy, typically as heat. Some non-limiting examples of dark or nonfluorescent quenchers include Dabcyl, Black Hole Quenchers, Iowa Black, QSY-7, AbsoluteQuencher, Eclipse non-fluorescent quencher, certain metallic particles such as gold nanoparticles, and the like. Certain dual-labeled probes comprising fluorophore-quencher pairs can emit fluorescence when the members of the pair are physically separated, for example but without limitation, nuclease probes such as TaqMan® probes. Other dual-labeled probes comprising fluorophore-quencher pairs can emit fluorescence when the members of the pair are spatially separated, for example but not limited to hybridization probes such as molecular beacons or extension probes such as Scorpion primers, Fluorophore-quencher pairs are well known in the art and used extensively for a variety of reporter probes (see, e.g., Yeung et al., BioTechniques 36:266-75, 2004; Dubertret et al., Nat. Biotech. 19:365-70, 2001; and Tyagi et al., Nat. Biotech, 18:1191-96, 2000).

In this application, a statement that one sequence is the same as, substantially the same as, complementary to, or substantially complementary to another sequence encompasses situations where both of the sequences are completely the same as, substantially the same as, or complementary or substantially complementary to one another, and situations where only a portion of one of the sequences is the same as, substantially the same as, complementary to, or substantially complementary to a portion or the entire other sequence.

U.S. Pat. No. 6,605,451 (Marmaro and Gerdes); U.S. Patent Application Publication Nos. 2004/0175733 A1 (Andersen and Ruff) and 2005/0266418 A1 (Chen and Ridzon); U.S. Application Ser, No. 10/944,153 (Lao and Straus); and Dolganov et al., Genome Research 11:1473-83, 2001 are incorporated by reference in their entirety for any purpose.

The term "marker" as used herein refers to a nucleic acid sequence, such as a gene, that is included in a panel because it is differentially expressed in one or more sample types. The term "marker amplicon" or "amplicon" refers to the nucleic acid sequence that is being amplified and analyzed to aid in the identification of the sample from which expressed RNA was obtained, In certain embodiments, one can identify or tentatively identify a sample based on the expression profile of the markers in the panel. Typically, a mRNA and/or miRNA is amplified according to the current teachings and its expression level is determined. By comparing the expression level of at least some of the markers in a panel of the current teachings, the sample can be identified. An amplicon can be double-stranded, single-stranded, or partially double-stranded and partially single-stranded, including without limitation, the separated component strands obtained from a double-stranded amplification product.

As used herein, the terms "polynucleotide", "oligonucleotide", and "nucleic acid" are used interchangeably and refer to single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine or possibly 5-methyldeoxycytosine (5mC), "G" denotes deoxyguanosine, "T" denotes thymidine, and "U" denotes deoxyuridine, unless otherwise noted.

Certain oligonucleotides of the current teachings can be synthesized using well-known chemical synthesis methods. Detailed descriptions of such techniques can be found in, among other places, Current Protocols in Nucleic Acid Chemistry, Beaucage et al., eds., John Wiley & Sons, New York, N.Y., including updates through May 2006; and Nucleic Acids in Chemistry And Biology, 2d ed., Blackburn and Gait, eds., Oxford University Press, 1996. Automated DNA synthesizers useful for synthesizing target regions and primers are commercially available from numerous sources, including for example, the Applied Biosystems DNA Synthesizer Models 381A, 391, 392, and 394 (Applied Biosystems, Foster City, Calif.), Oligonucleotides can also be generated biosynthetically, using in vivo methodologies and/or in vitro methodologies that are well known in the art. Descriptions of such technologies can be found in, among other places, Sambrook et al., Molecular Cloning, A Laboratory Manual, Cold Spring Harbor Press (1989) (hereinafter "Sambrook et al.");

and Current Protocols in Nucleic Acid Chemistry, Beaucage et al., eds., John Wiley & Sons, including updates through May 2006.

The term "primer" refers to a polynucleotide that selectively hybridizes to a marker or to a corresponding primer-binding site of an amplification product; and allows the synthesis of a sequence complementary to the corresponding polynucleotide template from its 3' end. In certain embodiments, a looped linker primer, sometimes referred to as a linker probe, is used as a reverse marker-specific primer, particularly when miRNA markers are to be amplified.

A "marker-specific primer pair" of the current teachings comprises a forward marker-specific primer and a corresponding reverse marker-specific primer. In some embodiments and under suitable conditions, a marker-specific primer pair allows for exponential amplification of the marker and/or marker amplicon. In certain embodiments, the reverse marker-specific primer is employed in a reverse transcription to generate a cDNA copy of the corresponding mRNA or corresponding miRNA in the sample. In certain embodiments, at least one such primer of a primer pair comprises a universal primer-binding site to allow for a universal primer to be employed in subsequent amplifications. In some embodiments, the forward target-specific primer and/or the reverse marker-specific primer further comprises an upstream tail portion that serves as a primer-binding site for an additional primer, for example but not limited to, a universal primer. In certain embodiments, at least one forward marker-specific primer, at least one reverse marker-specific primer, or at least one forward marker-specific primer and at least one reverse marker-specific primer further comprises at least one of: a reporter probe-binding site, an additional primer-binding site, and a reporter group, for example but not limited to a fluorescent reporter group. In certain embodiments, a forward primer and the corresponding reverse primer of a marker-specific primer pair and/or a universal primer pair have different melting temperatures (Tm) to permit temperature-based asymmetric PCR.

A variety of methods are available for obtaining nucleic acid from a sample. In certain embodiments, total nucleic acid, total, RNA, mRNA, or small RNA (including without limitation miRNA) are obtained. The method by which the desired nucleic acid population or subpopulation is obtained from the sample is not a limitation of the current teachings, provided that reasonably high quality nucleic acid is obtained. Commercially available nucleic acid extraction systems include, among others, the flashPAGE™ Fractionation System (Ambion) and the ABI PRISM® 6100 Nucleic Acid PrepStation and the ABI PRISM® 6700 Nucleic Acid Automated Work Station (Applied Biosystems); and nucleic acid sample preparation reagents and kits are also commercially available, including, RiboPure™, RNAqueous®, mirVana™ PARIS kit, and mirVana™ miRNA Isolation kit (Ambion) and Total RNA Isolation Chemistry Kit (P/N 4328773), ABI PRISM® TransPrep Chemistry Reagents, and NucPrep® Chemistry Reagents (Applied Biosystems).

The terms "amplifying" and "amplification" are used in a broad sense and refer to any technique by which a target region, an amplicon, or at least part of an amplicon, is reproduced or copied (including the synthesis of a complementary strand), typically in a template-dependent manner, including a broad range of techniques for amplifying nucleic acid sequences, either linearly or exponentially. Some non-limiting examples of amplification techniques include primer extension, including the polymerase chain reaction (PCR), RT-PCR, asynchronous PCR (A-PCR), and asymmetric PCR, strand displacement amplification (SDA), multiple displacement amplification (MDA), nucleic acid strand-based amplification (NASBA), rolling circle amplification (RCA), transcription-mediated amplification (TMA), and the like, including multiplex versions and/or combinations thereof. Descriptions of certain amplification techniques can be found in, among other places, Molecular Cloning, A Laboratory Manual, Cold Spring Harbor Press, 3d ed., 2001 (hereinafter "Sambrook and Russell"); Sambrook et al.; Ausubel et al.; PCR Primer: A Laboratory Manual, Diffenbach, Ed., Cold Spring Harbor Press (1995); Msuih et al., J. Clin. Micro. 34:501-07 (1996); PCR The Basics, 2d ed., McPherson & Møller, Taylor & Francis (2006; hereinafter "McPherson"); Nucleic Acid Protocols Handbook, Rapley, Humana Press (2000), Totowa, N.J. (hereinafter "Rapley"); U.S. Pat. Nos. 6,027,998 and 6,511,810; PCT Publication Nos. WO 97/31256 and WO 01/92579; Ehrlich et al., Science 252: 1643-50 (1991); Favis et al., Nature Biotechnology 18:561-64 (2000); Protocols & Applications Guide, rev. 9/04, Promega, Madison, Wis.; and Rabenau et al., Infection 28:97-102 (2000).

In certain embodiments of the instant teachings, an amplification reaction comprises at least one cycle of amplification, for example, but not limited to, the steps of: selectively hybridizing a primer to a marker sequence or an amplicon (or complements of either, as appropriate); synthesizing a strand of nucleotides in a template-dependent manner using a polymerase; and denaturing the resulting nucleic acid duplex to separate the strands. The cycle may or may not be repeated.

Amplification can comprise thermocycling or can be performed isothermally. In some embodiments, amplifying comprises a thermocycler, for example but not limited to a GeneAmp® PCR System 9700, 9600, 2700, or 2400 thermocycler (all from Applied Biosystems). In certain embodiments, single-stranded a plicons are generated in an amplification reaction, for example but not limited to asymmetric PCR or A-PCR.

Primer extension according to the present teachings is an amplification process comprising elongating a primer that is annealed to a template in the 5' to 3' direction using a suitable polymerase. According to certain embodiments, with appropriate buffers, salts, pH, temperature, and appropriate NTPs, a suitable polymerase can incorporate nucleotides complementary to the template strand starting at the 3'-end of an annealed primer, to generate a complementary strand. In certain embodiments, a DNA polymerase is used for primer extension lacks or substantially lacks 5'-exonuclease activity, 3'-exonuclease activity, or both. In some embodiments, primer extension comprises reverse transcription and the DNA polymerase comprises a RNA-dependent DNA polymerase, such as a reverse transcriptase, or a DNA-dependent DNA polymerase that under certain conditions comprises reverse transcriptase activity, for example but not limited to, *Thermus thermophilus* (Tth) DNA polymerase, recombinant Tth DNA polymerase (rTth), or *Thermus* species Z05 (T705) DNA polymerase (see, e.g., Smith et al., in PCR Primer, at pages 211-219). In certain embodiments, a reverse transcriptase that exhibits DNA-dependent DNA polymerase activity under suitable conditions, including but not limited to AMV reverse transcriptase is employed. In certain embodiments, primer extension comprises a RNA-dependent DNA polymerase and a DNA-dependent DNA polymerase. Descriptions of certain primer extension reactions can be found in, among other places, Sambrook et al., Sambrook and Russell, and Ausubel et al.

In certain embodiments, an amplification reaction comprises multiplex amplification, in which a multiplicity of different markers, a multiplicity of different marker amplicons, or both, are simultaneously amplified using a multiplicity of different primer pairs (see, e.g., Henegariu et al., BioTechniques 23:504-11, 1997; and Rapley, particularly in Chapter 79). Certain embodiments of the disclosed methods comprise a multiplex amplification reaction and a single-plex amplification reaction, including a multiplicity of single-plex reactions performed in parallel (see, e.g., U.S. Pat. No. 6,605,451 (Marmaro and Gerdes); U.S. Patent Application Publication No. 2004/0175733 A1 (Andersen and Ruff); and Dolganov et al., Genome Research 11:1473-83, 2001).

In certain embodiments, an amplifying reaction comprises asymmetric PCR. According to certain embodiments, asymmetric PCR comprises an amplification composition comprising (i) at least one primer pair in which there is an excess of one primer, relative to the corresponding primer of the primer pair, for example but not limited to a five-fold, a ten-fold, or a twenty-fold excess; (ii) at least one primer pair that comprises only a forward primer or only a reverse primer; (iii) at least one primer pair that, during given amplification conditions, comprises a primer that results in amplification of one strand and a corresponding primer that is disabled; or (iv) at least one primer pair that meets the description of both (i) and (iii) above, Consequently, when the marker or an amplification product is amplified, an excess of one strand of the subsequent amplification product (relative to its complement) is generated. Descriptions of asymmetric PCR, can be found in, among other places, McPherson, particularly in Chapter 5; and Rapley, particularly in Chapter 64.

In certain embodiments, one may use at least one primer pair wherein the melting temperature ($Tm_{50}$) of one of the primers is higher than the $Tm_{50}$ of the other primer, sometimes referred to as A-PCR (see, e.g., Published U.S. Patent Application No. US 2003-0207266 A1), In certain embodiments, the $Tm_{50}$ of the forward primer is at least 4-15° C. different from the $Tm_{50}$ of the corresponding reverse primer. In certain embodiments, the $Tm_{50}$ of the forward primer is at least 8-15° C. different from the $Tm_{50}$ of the corresponding reverse primer. In certain embodiments, the $Tm_{50}$ of the forward primer is at least 10-15° C. different from the $Tm_{50}$ of the corresponding reverse primer. In certain embodiments, the $Tm_{50}$ of the forward primer is at least 10-12° C. different from the $Tm_{50}$ of the corresponding reverse primer. In certain embodiments, in at least one primer pair, the $Tm_{50}$ of a forward primer differs from the $Tm_{50}$ of the corresponding reverse primer by at least about 4° C., by at least about 8° C., by at least about 10° C., or by at least about 12° C.

In certain embodiments of A-PCR, in addition to the difference in $Tm_{50}$ of the primers in a primer pair, there is also an excess of one primer relative to the other primer in the primer pair. In certain embodiments, there is a five- to twenty-fold excess of one primer relative to the other primer in the primer pair. In certain embodiments of A-PCR, the primer concentration is at least 50 nM.

In A-PCR according to certain embodiments, one may use conventional PCR in the first cycles of amplification such that both primers anneal and both strands of a double-stranded amplicon are amplified. By raising the temperature in subsequent cycles of the same amplification reaction, however, one may disable the primer with the lower $T_m$ such that only one strand is amplified. Thus, the subsequent cycles of A-PCR in which the primer with the lower $T_m$ is disabled result in asymmetric amplification. Consequently, when the target region or an amplification product is amplified, an excess of one strand of the subsequent amplification product (relative to its complement) is generated.

According to certain embodiments of A-PCR, the level of amplification can be controlled by changing the number of cycles during the first phase of conventional PCR cycling. In such embodiments, by changing the number of initial conventional cycles, one may vary the amount of the double-stranded amplification products that are subjected to the subsequent cycles of PCR at the higher temperature in which the primer with the lower $T_m$ is disabled.

Certain methods of optimizing amplification reactions are known to those skilled in the art. For example, it is known that PCR may be optimized by altering times and temperatures for annealing, polymerization, and denaturing, as well as changing the buffers, salts, and other reagents in the reaction composition. Optimization may also be affected by the design of the primers used. For example, the length of the primers, as well as the G-C:A-T ratio may alter the efficiency of primer annealing, thus altering the amplification reaction. Descriptions of amplification optimization can be found in, among other places, James G. Wetmur, "Nucleic Acid Hybrids, Formation and Structure," in Molecular Biology and Biotechnology, pp. 605-8, (Robert A. Meyers ed., 1995); McPherson, particularly in Chapter 4; Rapley; and Protocols & Applications Guide, rev, 9/04, Promega.

In some embodiments, unincorporated primers, unincorporated dNTPs, amplification reagents, or combinations thereof, are separated from an amplification product by, for example but not limited to, gel or column purification, sedimentation, filtration, beads, including streptavidin-coated beads, magnetic separation, or hybridization-based pull out, including annealing amplification products comprising hybridization tags to a solid support. A number of kits and reagents for performing such separation techniques are commercially available, including the Wizard® MagneSil™ PCR Clean-Up System (Promega), the MinElute PCR Purification Kit, the QIAquick Gel Extraction Kit, the QIAquick Nucleotide Removal Kit, the QIAquick 96 PCR Purification Kit or BioRobot Kit (all from Qiagen, Valencia, Calif.), Dynabeads® (Dynal Biotech), or the ABI PRISM® Duplex™ 384 Well F/R Sequence Capture Kit (Applied Biosystems P/N 4308082). In some embodiments, an amplification product is not purified prior to a subsequent amplifying reaction.

In certain embodiments, the disclosed methods and kits comprise a solid support. Non-limiting examples of solid supports include, agarose, sepharose, polystyrene, polyacrylamide, glass, membranes, silica, semiconductor materials, silicon, organic polymers; optically identifiable micro-cylinders; biosensors comprising transducers; appropriately treated or coated reaction vessels and surfaces, for example but not limited to, micro centrifuge or reaction tubes, wells of a multiwell microplate, and glass, quartz or plastic slides and/or cover slips; and beads, for example but not limited to magnetic beads, paramagnetic beads, polymer beads, metallic beads, dye-impregnated or labeled beads, coated beads, glass beads, microspheres and nanospheres. In some embodiments, a solid support is used in a separating and/or detecting step, for example but not limited to, for purifying and/or analyzing amplification products. Those in the art will appreciate that any number of solid supports may be employed in the disclosed methods and kits and that the shape and composition of the solid support is generally not limiting. It is to be appreciated that a solid support may be porous or non-porous, and may have a smooth or even surface or an irregular or uneven surface. In certain embodiments, a solid support comprises a microarray, a bead array, or a bead for use in a flow cytometric assay (see, e.g., Shingara et al., RNA 11:1461-70, 2005: Lu et al., Nature 435(9):834-38, 2005). A variety of exemplary arrays and bead-based systems for use in the current teachings are commercially available from, among other sources, Applied Biosystems; Ambion, Austin, Tex.; Illumina, San Diego, Calif.; Affymetrix, Sunnyvale, Calif.; and Luminex, Austin, Tex.

In some embodiments, the methods of the current teachings comprise a Q-PCR reaction. The term "quantitative PCR", or "Q-PCR" refers to a variety of methods used to quantify the results of the polymerase chain reaction for specific nucleic acid sequences. Such methods typically are categorized as kinetics-based systems, that generally determine or compare the amplification factor, such as determining the threshold cycle ($C_t$), or as co-amplification methods, that generally compare the amount of product generated from simultaneous amplification of target and standard templates. Many Q-PCR techniques comprise reporter probes, nucleic acid dyes, or both (see, e.g., Kubista et al., Mol. Aspects of Med. 27 (2-3):95-125 (2006)). For example but not limited to TaqMan® probes (Applied Biosystems), i-probes, molecular beacons, Eclipse probes, scorpion primers, Lux™ primers, FRET primers, ethidium bromide, SYBR® Green I (Molecular Probes), ethidium bromide. BOXTO (TATAA Biocenter AB), and PicoGreen (Molecular Probes).

In some embodiments, the disclosed methods and kits comprise a microfluidics device, "lab on a chip", or micrototal analytical system (μTAS). In some embodiments, sample preparation is performed using a microfluidics device. In some embodiments, an amplification reaction is performed using a microfluidics device. In some embodiments, a Q-PCR reaction is performed using a microfluidic device, for example but not limited to a TaqMan® Low Density Array card (Applied Biosystems). Descriptions of exemplary microfluidic devices can be found in, among other places, Published PCT Application Nos. WO1085341 and WO 04/011666; Kartalov and Quake, Nucl. Acids Res. 32:2873-79, 2004; and Fiorini and Chiu, BioTechniques 38:429-46, 2005.

A "panel of markers" or "panel" is a select group of genes that are differentially expressed in various tissues or that are present in characteristic levels in specific body fluids, such that by determining the mRNA and/or miRNA expression profile of a tissue or body fluid sample for at least some of the markers in the panel, one can determine the identity of the sample, for example but not limited to, saliva, blood, brain, or muscle. Those in the art will understand that different tissues, cell types, and body fluids have defined sets of highly expressed or uniquely expressed genes and instructed by the current teachings, will appreciate that these distinctive expression patterns can be useful in identifying the tissue or body fluid from which the nucleic acid was obtained. It will also be appreciated by those in the art that additional markers for inclusion in such panels can be identified by routine expression analysis methods, wherein the expression profiles of various tissues or body fluids are compared with each other. Exemplary panels of markers useful for identifying human samples are shown in Tables 1-3.

In certain embodiments, an amplification reaction comprises multiplex amplification, in which a multiplicity of different target nucleic acids and/or a multiplicity of different amplification product species are simultaneously amplified using a multiplicity of different primer pairs. Certain embodiments of the disclosed methods comprise a two step amplification comprising a multiplex amplification reaction and a single-plex amplification reaction, including a multiplicity of single-plex or lower-plexy reactions (for example but not limited to a two-plex, a three-plex, a four-plex, a five-plex, or a six-plex reaction) performed in parallel. In certain embodiments, the multiplex first amplification reaction comprises a reverse transcription reaction or a reverse transcription reaction is performed followed by a multiplex first amplification reaction. In certain embodiments, a multiplex first amplification reaction is performed for a limited number of cycles, for example but not limited to 5 cycles, 6 cycles, 7 cycles, 8 cycles, 9 cycles, 10 cycles, 11 cycles, 12 cycles, 13 cycles, 14 cycles, 15 cycles, 16 cycles, 17 cycles, 18 cycles, 19 cycles, 20 cycles, 21 cycles, 22 cycles, 23 cycles, 24 cycles, or 25 cycles. In certain embodiments, a parallel single-plex second amplification reaction comprises a microfluidics device, for example but not limited to a TaqMan® Low Density Array (Applied Biosystems).

In certain embodiments, one or more markers are amplified, for example by the reverse-transcription polymerase chain reaction ("RT-PCR"), using a plurality of amplification primer pairs, each of which is suitable for amplifying a different marker and/or marker amplicon. Because a plurality of different marker sequences are amplified simultaneously in a single reaction, the multiplex amplifications may be used in a variety of contexts to effectively increase the concentration or quantity of a sample available for downstream analyses and/or assays. Once the sample has been multiplex amplified according to the methods described herein, it may be divided into aliquots, with or without prior dilution, for subsequent analyses. Owing to its increased concentration and quantity, significantly more analyses or assays can be performed with the multiplex amplified sample than could have been performed with the original sample. In many embodiments, multiplex amplification even permits the ability to perform assays or analyses that require more sample, or a higher concentration of sample, than was originally available. For example, after a 1000×multiplex amplification, subsequent assays could then be performed at 1000×less sample volume.

Certain embodiments of the instant methods comprise an RT reaction followed by a two-step amplification reaction. In a first step, a plurality of different target sequences in a panel of markers are multiplex amplified by PCR in the presence of a plurality of different amplification primer pairs or sets, generating a plurality of different first amplification products. In certain embodiments, in a second step the diluted or undiluted multiplex amplification product is divided into a plurality of reaction vessels, one of the first amplification products in each vessel is single-plex amplified in the presence of a set of amplification primers for amplifying that first amplification product (such as a marker amplicon) and the single-plex amplifications monitored for the accumulation of second amplification product. In certain such embodiments, the second amplification reaction further comprises a reporter probe, a nucleic acid dye, a reference dye, or combinations thereof. In certain embodiments, a small number of first amplification products in each vessel, e.g., 2, 3, 4, 5, or 6 different first amplification products, are amplified in the presence of a set of amplification primers suitable for amplifying each of the desired first amplification products and the amplifications monitored for the accumulation of second amplification products.

The accumulation of single-plex amplification product can be monitored at the end of the reaction by conventional means, e.g., by chromatography, by eletrophoresis, by binding a nucleic acid dye, or by binding certain reporter probes. Alternatively, the accumulation of single-plex amplification product can be monitored as a function of time using well known methods, such as carrying out the single-plex amplification in the presence of one or more dyes or labels capable of producing a detectable signal upon binding double-stranded polynucleotide (e.g., SYBR® Green I or II, SYBR® Gold, ethidium bromide, or YO-PRO-1; Molecular Probes, Eugene, Oreg.) or an oligonucleotide probe labeled with a suitable labeling system (e.g. a TaqMan® probe, or other suitable detector probe). The accumulation of a small number of different second amplification products (e.g., 2, 3, 4, 5, or 6) in the same reaction well or chamber can be monitored as a function of time using a reporter probe for each of the second amplification products, wherein each of the different reporter probes will, under suitable conditions, emit a fluorescent wavelength that can be distinguished from the other reporter probes.

Certain Exemplary Kits

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. Preferably, the kit components are optimized to operate in conjunction with one another.

In certain embodiments, kits comprise a first DNA polymerase, a multiplicity of different primer pairs, wherein each of the different primer pairs is designed to amplify a target sequence of one marker of a panel of markers or a control sequence. For example but not as a limitation, a kit designed to amplify a panel of six different markers would comprise at least six different primer pairs, at least one for each of the six markers. In certain embodiments, kits further comprise a second DNA polymerase. In some embodiments, kits comprise an amplification primer pair. In some embodiments, a primer pair comprises a linker probe (see Chen and Ridzon, U.S. Patent Application Publication No, 2005/0266418 A1) a forward primer, a reverse primer, any of which in some embodiments comprise a universal priming sequence or the complement of a universal priming sequence. In certain embodiments, kits comprise at least one universal primer. In some embodiments, kits comprise a forward primer, a reverse primer, or a forward primer and a reverse primer that further comprises a reporter group. In some such embodiments, the reporter group of a forward primer of a primer pair is different from the reporter group of the reverse primer of the primer pair. In some embodiments, kits further comprise at least one of: a reverse transcriptase; a reporter probe; a nucleic acid dye; a reporter group; a control sequence, for example but not limited to an internal positive control, such as a housekeeping gene; and a polynucleotide ladder comprising molecular size or weight standards. In certain embodiments, kits comprise at least one reporter probe for each amplicon derived from a marker on the panel being evaluated.

EXEMPLARY EMBODIMENTS

Panels of Markers

The methods of the current teachings employ primer pairs corresponding to markers from specific panels of markers to generate appropriate gene expression profiles which are compared to the expression profile for those markers from known tissues and body fluids to identify the sample. The markers are typically selected for inclusion in a particular panel because they represent genes that are differentially expressed in a tissue or body fluid of interest, for example but not limited to, a certain tissue or body fluid that may be encountered at a crime scene. The panels of the current teachings comprise mRNA markers or miRNA markers. Certain panels of the current teachings comprise at least one mRNA markers and at least one miRNA marker. In some embodiments, the disclosed panels further comprise control markers such as housekeeping genes or other internal control sequences.

An illustrative panel of the current teachings comprises: (a) at least one marker for saliva, wherein the at least one saliva marker comprises at least one of PRB4, PRB1, STATH, PRB3, and HTN3; (b) at least one marker for semen, wherein the at least one semen marker comprises at least one of SEMG1, SEMG2, TGM4, MCSP, PRM1, and PRM2; (c) at least one marker for saliva containing mucus, wherein the at least one saliva containing mucus marker comprises at least one of PRB1, PRB3, and PRB4; and (d) at least one marker for vaginal secretions, wherein the at least one vaginal secretion marker comprises at least one of MUC4 and ESR1. In certain embodiments, the panel further comprises: (e) at least one marker for blood, wherein the at least one blood marker comprises at least one of ANK1, SPTB, and PBGD; (f) at least one marker for menstrual blood, wherein the at least one menstrual blood marker comprises MMP11; or (g) at least one marker for blood, wherein the at least one blood marker comprises at least one of ANK1, SPTB, and PBGD; and at least one marker for menstrual blood, wherein the at least one menstrual blood marker comprises MMP11.

In certain embodiments, a panel of markers comprises PRB4, PRB1, STATH, SEMG1, SEMG2, TGM4, MCSP, ANK1, SPTB, PBGD, MUC4, ESR1, and MMP11. In some embodiments, the panel further comprises at least one of: PRB3, HTN3, PRM1, PRM2, PRB1, and PRB3.

Certain mRNA marker panels of the current teachings comprise groups of markers comprise: (a) hCG1816257; (b) MMP11; (c) at least one of UGT148, hCG2017793, APCS, and FGB; (d) at least one of PNLIPRP1, REG1B, hCG2042161, and PRSS3; (e) TGM4; (f) FLJ46026; (g) at least one of TH, FDX1, and QPCT; (h) at least one of hCG2040797 and KLK3; (i) at least one of PRM1, PRM2, MGC42718, SPA 17, and MCSP; (j) at least one of PRB1, PRB3, and PRB4; (k) LGALS4; (l) at least one of PGA5 and PGC; (m) at least one of SEMG1, SEMG2, and CYSLTR2; (n) at least one of ANKRD1 and hCG1813636.1; (O) ANK1; (p) TNNI1; and (q) PMP2. Certain panel embodiments comprise: at least one marker from five of these groups (i.e., groups (a) through (q) above); at least one marker from six of these groups; at least one marker from seven of these groups; at least one marker from eight of these groups; at least one marker from nine of these groups; at least one marker from ten of these groups; at least one marker from eleven of these groups; at least one marker from twelve of these groups; at least one marker from thirteen of these groups; at least one marker from fourteen of these groups; at least one marker from fifteen of these groups; at least one marker from sixteen of these groups; or at least one marker from each of these groups.

Certain miRNA marker panels comprise: at least brain marker comprising at least one of miR-125b, miR-128a, miR-128b, miR-129, miR-135, and miR-153; at least one muscle marker comprising at least one of miR-1d, miR-133a, miR-133b, miR-296, miR-208; at least one kidney marker comprising at least one of miR-192, miR-204, miR-215, and miR-216; at least one thymus marker comprising at least one of miR-96 and miR-182; at least one testes marker comprising at least one of miR-10b and let-7e; at least one placenta marker comprising at least one of miR-141 and miR-23a; or combinations thereof.

Some panel embodiments of the current teachings comprise at least one mRNA marker and at least one miRNA marker selected from Tables 1 and 3; Tables 2 and 3; or Tables 1, 2, and 3. Certain marker panel embodiments comprise a multiplicity of markers selected form Table 1, a multiplicity of markers selected form Table 2, or a multiplicity of markers selected form Table 3.

Exemplary Method Embodiments

According to certain methods of the current teachings, the nucleic acid from a forensic sample is obtained using any suitable method known in the art. The nucleic acid is combined with a DNA polymerase and a set of different marker-specific primers, where each marker-specific primer is designed to amplify one of the markers in the panel of interest, to form a reaction composition. In certain embodiments, the reaction composition further comprises a linker probe. For illustration purposes but not as a limitation, the set of marker-specific primers for a panel comprising fifteen different markers would include at least fifteen different primers. Typically, the set of different marker-specific primers comprises a set of different marker-specific primer pairs, each comprising a forward and a reverse marker-specific primer. In some embodiments, the DNA polymerase comprises a DNA-dependent DNA polymerase and/or an RNA-dependent DNA polymerase, for example, a reverse transcriptase. In some embodiments, the DNA polymerase comprises a DNA-dependent DNA polymerase that, under certain conditions, polymerizes reverse transcription, for example but not limited to Tth DNA polymerase. In yet other embodiments, the DNA polymerase comprises a RNA-dependent DNA polymerase with both reverse transcription and DNA-dependent DNA polymerase activity, for example but not limited to, certain retroviral reverse transcriptases such as AMV RT.

The reaction composition is incubated under conditions suitable for reverse transcription to occur and cDNA is generated. The cDNA is amplified by PCR to generate an expression profile. In some embodiments, the gene expression profile is generated using conventional RT-PCR techniques, including without limitation, qRT-PCR techniques known in the art. In certain embodiments, the PCR comprises a two step reaction, for example but not limited to, the method of Anderson and Ruff (U.S. Patent Application Publication No, US 2004/0175733 A1). The expression profile is compared to known expression profiles obtained from know (control) body fluids and tissues. Based on this comparison, the sample can be identified.

In one illustrative method, a body fluid stain from a crime scene is rehydrated and suspended in an appropriate buffer. Total RNA is extracted from the rehydrated body fluid and combined in a reaction mixture comprising rTth DNA polymerase, a mix of dNTPs, $Mn(OAc)_2$, and the following ten primer pairs: Hs00864002_m1, Hs00818764_m1, Hs00162389, Hs00268141_m1, Hs00268143_m1, Hs00165820_m1, Hs00609297_m1, Hs00366414_m1, Hs00174860_m1, and Hs00171829_m1 (available from Applied Biosystems). These primer pairs correspond to a panel of body fluid markers comprising markers for saliva, semen, blood, vaginal secretion and menstrual blood (see, e.g., Table 1). The reaction mixture is incubated under conditions suitable for cDNA to be produced, then the reaction mixture is thermocycled for twenty cycles to generate marker amplicons. The thermocycled reaction mixture is diluted tenfold, then divided into ten wells of a 384 well micro-card, wherein each such well comprises a reporter probe designed to anneal with one of the ten marker amplicons and the corresponding primer pair for amplifying that marker amplicon. The plate is loaded into an Applied Biosystems 7900HT Fast Real-Time PCR System and thermocycled. The single-plex amplifications are monitored in real-time for the accumulation of amplification products to generate an expression profile for this ten marker panel. The resulting expression profile is compared with the expression profiles obtained for saliva, semen, blood, vaginal secretion, and menstrual blood to determine whether the sample can be identified.

In another exemplary method embodiment, the small RNA is obtained from a tissue sample obtained from a crime scene using a mirVana miRNA Isolation Kit (Ambion). The isolated RNA is combined in a reaction mixture comprising Multi-Scribe™ reverse transcriptase (Applied Biosystems), Ampli-Taq Gold DNA polymerase, a mix of dNTPs, and twelve primer pairs comprising a linker probes and corresponding forward primer for each marker of a human miRNA panel selected from Table 3, consisting of hsa-mir-129, hsa-mir-135, hsa-mir-1d, hsa-mir-133b, hsa-mir-296, hsa-mir-192, hsa-mir215, hsa-mir-376, hsa-mir-148, hsa-mir-208, hsa-mir-182, and hsa-mir-10b (see miRBase miRNA database at the http site: microrna.sanger/ac/uk for miRNA sequences). Alternatively, primer sets comprising unconventionally short target-binding portions (see, Lao and Straus, U.S. patent application Ser. No. 10/944,153) designed to amplify the markers of this exemplary miRNA panel can be used in the reaction mixture in place of the primer pairs comprising linker probes, described above. The reaction composition is incubated under conditions suitable for generating complementary DNA and then a first PCR amplification step is performed for twenty-five cycles.

The reaction mixture is diluted and divided into twelve aliquots that are transferred into wells of a 96-well plate that each contain a primer pair suitable for amplifying one marker amplicon and the nucleic acid dye Sybr® Green I. The plate is thermocycled and the accumulation of single-plex amplification is monitored after each cycle to generate an expression profile for the exemplary twelve marker miRNA panel. The resulting expression profile is compared with the expression profiles obtained with brain, muscle, kidney, pancreas, liver, heart, thymus, and testes, to determine whether the tissue sample can be identified.

Those in the art will appreciate that these two exemplary methods of the current teachings illustrate the use of marker panels to identify a forensic sample based on its gene expression profile relative to corresponding expression profiles from known tissues and body fluids.

Exemplary Kit Embodiments

The instant teachings also provide kits designed to expedite performing the subject methods. Kits serve to expedite the performance of the methods of interest by assembling two or more components required for carrying out the methods. Kits preferably contain components in pre-measured unit amounts to minimize the need for measurements by end-users. Kits preferably include instructions for performing one or more of the disclosed methods. Preferably, the kit components are optimized to operate in conjunction with one another.

The instant kits comprise at least one primer pair for each marker in a panel of markers, a DNA polymerase, a dNTP mixture, and optionally a polymerase-compatible source of manganese ions. Certain kits further comprise a reporter probe species for each marker amplicon, a reaction vessel, and a nucleic acid dye.

The current teachings, having been described above, may be better understood by reference to examples. The following examples are intended for illustration purposes only, and should not be construed as limiting the scope of the teachings herein in any way.

Example 1

Exemplary Nucleic Isolation Technique

Nucleic acid is isolated from a sample using PrepMan chemistry (Applied Biosystems) and a spin column comprising a membrane as follows. Ten to thirty microliters (µL) of liquid sample (e.g., saliva or blood) is combined with reaction mix to a final volume of 100 µL, where the reaction mix includes 50 µL 2×LYS buffer (20 mM Tris (pH 7.4), 2 mM EDTA (pH 8.0), 5% Triton X-100, 150 mM NaCl), 4.0-24.0 µL DEPC treated water (Ambion, Austin Tex.; combined water and sample volume equals 34.0 µL), 3 µL PolyA RNA (200 ng/µL, Sigma-Aldrich, St. Louis, Mo.), and 8 µL glycogen (5 µg/µl, Ambion) in a 1.5 mL MicroAmp tube (Applied Biosystems). To this suspension is added 100 µL 2× ncRNA buffer (Applied Biosystems) and the tube is mixed by vortexing on a Baxter Scientific vortex for approximately one minute. Optionally, the solution is passed through a 20-gauge (or higher) needle (0.9 mm diameter) fitted to a sterile syringe. The sample is incubated for ten minutes at room temperature, then 400 µL of freshly prepared DNA precipitation solution (100 µL DNA precipitation solution 1 mixed with 300 µL DNA precipitation solution 2 (Applied Biosystems P/Ns 4325962 and 4325964, respectively) is added to the tube.

A 1× ncRNA buffer solution is prepared by combining 300 µL of 2× ncRNA buffer with an equal volume of DNA precipitation solution 2. A Whatman QMA membrane (part no. 1851047) is cut to size and placed into the inlet side of a spin column (Micro Bio-Spin chromatography column, Bio-Rad, Hercules Calif.). The spin column is placed in a 2 mL collection tube and the membrane is pre-wet with 40 µL of the 1× ncRNA lysis buffer. The sample, including any precipitate that may have formed, is placed in the top of the spin column assembly. The column is centrifuged for 30 seconds at about 8000×g to remove most of the liquid. The column containing nucleic acid from the sample is sequentially washed with 500 µL 1× ncRNA lysis buffer, 600 µL DNA wash solution 1 (Applied Biosystems PIN 4325958), and twice with 600 µL DNA wash solution 2 (Applied Biosystems P/N 4325960), with a 30 second centrifugation at about 8000×g between each wash step. The column is then centrifuged at about 10000×g for one minute.

The nucleic acid is eluted from the membrane by adding 30 µL elution solution (Applied Biosystems P/N 4305893) to the spin column, incubating for three minutes, centrifuging for thirty seconds at about 10000×g, and collecting the first eluate, The first eluate is placed back into the column and the procedure is repeated. The second eluate is used for nucleic acid analysis, including without limitation expression profiling. Those in the art will appreciate that while the foregoing example provides a method for isolating nucleic acid from a sample, a number of alternative nucleic acid isolation methods can be effectively employed in the disclosed methods, including but not limited to a variety of commercially available kits and reagents from among other sources, Ambion, Applied Biosystems, Qiagen, Stratagene, and Promega.

Example 2

Exemplary mRNA Profile Generation

A 2× RT master mix is prepared using the components of the High-Capacity cDNA Archive Kit (Applied Biosystems). For each sample to be evaluated, the master mix contains 3 µL 10× Reverse Transcription Buffer, 1.2 µL 25× dNTPs, 3 µL random primers, 1.5 µL MultiScribe™ Reverse Transcriptase (50 U/µL), and 6.3 µL nuclease-free water (15 µL for each sample). A 15 µL volume of the 2× RT master mix and 15 µL of the isolated nucleic acid from Example 1 are combined in a well of 96 well reaction plate (or a MicroAmp tube, as appropriate). The plate is sealed with adhesive film and briefly centrifuged. The plate is loaded onto a GeneAmp® PCR System 9700 thermal cycler, the cycling conditions are set at 25° C. for ten minutes, 37° C. for two hours, and then 4° C., and the reaction mixture in the plate is thermocycled to generate cDNA.

A pool of primers and corresponding nuclease probes for each marker in the panel to be evaluated is prepared by combining 5 µL of at least one Assay on Demand TaqMan® Gene Expression Assay (AOD, Applied Biosystems; each AOD assay comprising a dye-labeled TaqMan® MGB probe and a corresponding primer pair pre-designed for the marker) for each marker in the panel. The pool is then diluted with nuclease-free water so that each of the AODs is effectively diluted 1:50; for illustration purposes, an exemplary marker panel includes twenty different AODs in a pooled volume of 100 µL (20 AODs×5 µL/AOD), which is diluted to a final volume of 250 µL. For each cDNA to be pre-amplified, a pre-amplification reaction mix is formed by combining 25 µL TaqMan® Universal PCR Master Mix (P/N 4304437), 2.5 µL AmpliTaq Gold DNA polymerase (5 U/µL; P/N 4311816), 5 µL of the diluted AOD pool, and 15 µL nuclease free water (final volume 47.5 µL per cDNA).

A 47.5 µL volume of the pre-amplification mix and 2.5 µL of the previously generated cDNA are combined in a well of 96 well reaction plate. The plate is sealed with adhesive film, then the plate is vortexed for about ten seconds and briefly centrifuged. The plate is loaded onto a GeneAmp® PCR System 9700 thermal cycler (Applied Biosystems), the cycling conditions are set at 50° C. for two minutes, 95° C. for ten minutes, 10-15 cycles of 95° C. for fifteen seconds and 60° C. for four minutes, and then 4° C. The pre-amplification mixture in the plate is thermocycled to generate pre-amplified PCR product.

For each marker in the panel, a real-time PCR reaction is performed in wells of a 96 well. For illustration purposes, for a ten marker panel, each pre-amplified PCR product would be analyzed in ten different wells or the plate, each containing a different AOD corresponding to one of the markers of the panel. Controls, for example certain housekeeping genes such as GAPDH or β-actin may be included in additional wells, as desired. To each well of the reaction plate is added 25 µL TaqMan® Universal PCR Master Mix, No AmpErase® UNG (PIN 4324018), 2.5 µL of the appropriate AOD, 20 µL nuclease free water, and 2.5 µL of the pre-amplification product. The plate is sealed with adhesive film, then vortexed for about ten seconds and briefly centrifuged. Ten microliters of each of these reaction mixtures is robotically transferred (Beckman Multimek) to a corresponding well in each of the four quadrants of a 384 well plate, the plate is sealed with an adhesive film and briefly centrifuged. A real time PCR reaction is performed using an Applied Biosystems 7900HT Real-Time PCR System with a thermocycling profile of 50° C. for two minutes, 95° C. for ten minutes, forty cycles of 95° C. for fifteen seconds and 60° C. for one minute, and the integral data collection software determines the Ct values for each well. After the run has completed, the Ct data is extracted from the instrument, the ΔCt values are calculated, and the expression profile of the marker panel is generated for each sample that was evaluated. Based on the expression profile for a given sample, the identity of that sample is determined.

Those in the art will appreciate that a pre-amplification may not be necessary if the sample contains a sufficiently high marker copy number and that the nucleic acid isolated from such samples may be directly analyzed by real-time PCR to generate an expression profile for the marker panel. Those in the art will also appreciate that different mRNA and miRNA expression profiling techniques can be employed, for example but not limited to array analyses, including without limitation microarrays, bead arrays, and filter arrays (see, e.g. Shingara et al., RNA 11:1461-70 (2005); Castoldi et al., RNA 12:1-8 (2006); Sioud et al., BioTechniques 37:574-80 (2004); and Lu et al., Nature 435:834-38 (2005).

The methods, panels of markers, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, methods, and compositions, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

TABLE 1

Human Body Fluid Identification Panel (mRNA)

| Source | Symbol | Name | AOD No.[1] |
|---|---|---|---|
| Saliva | PRB3 | proline-rich protein BstNI subfamily 3 | Hs00818925_m1 |
| | PRB4 | proline-rich protein BstNI subfamily 4 | Hs00864002_m1 |
| | HTN3 | histatin3 | Hs00264790 |
| | PRB1 | proline-rich protein BstNI subfamily 1 | Hs00818764_m1 |
| | STATH | statherin | Hs00162389 |
| Semen | SEMG1 | semenogelin I | Hs00268141_m1 |
| | SEMG2 | semenogelin II | Hs00268143_m1 |
| | TGM4 | transglutaminase 4 (prostate) | Hs00162710_m1 |
| | PRM1 | Protamine 1 | Hs00358158_m1 |
| | PRM2 | Protamine 2 | Hs00172518_m1 |
| | MCSP | mitochondrial capsule selenoprotein | Hs00229076_m1 |
| Blood | ANK1 | ankyrin 1 | Hs00220867_m1 |
| | SPTB | Beta-spectrin | Hs00165820_m1 |
| | PBGD | Porphobilinogen deaminase | Hs00609297_m1 |
| Sputum | PRB1 | proline-rich protein BstNI subfamily 1 | Hs00818764_m1 |
| | PRB3 | proline-rich protein BstNI subfamily 3 | Hs00818925_m1 |
| | PRB4 | proline-rich protein BstNI subfamily 4 | Hs00864002_m1 |
| Vaginal secretion | MUC4 | mucin 4, tracheobronchial | Hs00366414_m1 |
| | ESR1 | estrogen receptor | Hs00174860_m1 |
| | MMP7 | matrix metallopeptidase 7 (matrilysin, uterine) | Hs00159163_m1 |
| Menstrual blood | MMP11 | matrix metallopeptidase 11 (stromelysin 3) | Hs00171829_m1 |

[1]Assays-On-Demand Gene Expression Product Numbers (Applied Biosystems, Foster City, CA)

TABLE 2

Human Tissue Identification Panel (mRNA)

| Source | Symbol | Name | AOD No.[2] |
|---|---|---|---|
| Ovary | hCG1816257 | | Hs01893192_s1 |
| Brain (Whole) | MMP11 | Metalloproteinase domain 11 | Hs00253742 |
| Kidney/Liver | UGT1A8 | UDP glycosyltransferase 1 family, polypeptide A8 | Hs01592482_m1 |
| Liver/fetal liver | hCG2017793 | Hs00860044_m1 | Hs00860044_m1 |
| | APCS | amyloid P component, serum | Hs00356632_g1 |
| | FGB | fibrinogen, B beta polypeptide | Hs00170586_m1 |
| Pancreas | PNLIPRP1 | pancreatic lipase-related protein 1 | Hs00173824_m1 |
| | REG1B | regenerating islet-derived 1 beta (pancreatic stone protein, pancreatic thread protein) | Hs00359614_g1 |
| | hCG2042161 | | Hs00975170_m1 |
| | PRSS3 | protease, serine, 3 (mesotrypsin) | Hs00605637_m1 |
| | PNGPRP1 | | |
| Prostate | TGM4 | transglutaminase 4 (prostate) | Hs00162710_m1 |
| Spleen | FLJ46026 | FLJ46026 protein | Hs01651932_m1 |
| Adrenal Gland | TH | tyrosine hydroxylase | Hs00165941_m1 |
| | FDX1 | ferredoxin 1 | Hs00759864_s1 |
| | QPCT | glutaminyl-peptide cyclotransferase (glutaminyl cyclase) | Hs00202680_m1 |
| Prostate | hCG2040797 | | Hs01394126_m1 |
| | KLK3 | kallikrein 3, (prostate specific antigen) | Hs00377590_s1 |
| Testis | PRM1 | Protamine 1 | Hs00358158_m1 |
| | PRM2 | Protamine 2 | Hs00172518_m1 |
| | MGC42718 | hypothetical protein MGC42718 | Hs00542901_m1 |
| | SPA17 | hypothetical protein MGC42718 | Hs00255619_m1 |
| Testis/ Epididymus | MCSP | mitochondrial capsule selenoprotein | Hs00229076_m1 |
| Throat/Trachea/Salivary Gland | PRB1 | proline-rich protein BstNI subfamily 1 | Hs00818764_m1 |
| | PRB3 | proline-rich protein BstNI subfamily 2 | Hs00818925_m1 |
| | PRB4 | proline-rich protein BstNI subfamily 4 | Hs00864002_m1 |
| Uterus/Trachea | MMP10 | Metalloproteinase domain 10 | Hs00233987_m1 |
| Small intestine, colon, duodenum, cecum | LGALS4 | lectin, galactoside-binding, soluble, 4 (galectin 4) | Hs00196223_m1 |
| Stomach/small intestine | PGA5 | pepsinogen 5, group I (pepsinogen A) | Hs00380569_m1 |
| Stomach | PGC | progastricsin (pepsinogen C) | Hs00160052_m1 |
| Ductus deferens/Seminal Vesicle | SEMG1 | semenogelin I | Hs00268141_m1 |
| | SEMG2 | semenogelin II | Hs00268143_m1 |
| | CYSLTR2 | cysteinyl leukotriene receptor 2 | Hs00252658_s1 |
| Fetal Heart | ANKRD1 | ankyrin repeat domain 1 (cardiac muscle) | Hs00173317_m1 |
| | hCG1813636.1 | | Hs01395395_m1 |
| Peripheral Blood/Throat | ANK1 | ankyrin 1 | Hs00220867_m1 |
| Skeletal Muscle | TNNI1 | troponin I, skeletal, slow | Hs00268531_m1 |
| Spinal Cord | PMP2 | peripheral myelin protein 2 | Hs00160204_m1 |

[2]Assays-On-Demand Gene Expression Product Numbers (Applied Biosystems, Foster City, CA)

TABLE 3

Human Tissue Identification Panel (miRNA)

| Source | Name |
| --- | --- |
| Brain | hsa-miR-125b |
| | hsa-miR-128a,b |
| | hsa-miR-129 |
| | hsa-miR-135 |
| | hsa-miR-153 |
| | hsa-miR-219 |
| Muscle (skeletal & heart) | hsa-miR-1d |
| | hsa-miR-133a,b |
| | hsa-miR-296 |
| Kidney | hsa-miR-192 |
| | hsa-miR-204 |
| | hsa-miR-215 |
| | hsa-miR-216 |
| Pancreas | hsa-miR-375 |
| | hsa-miR-376 |
| Liver | hsa-miR-122a |
| | hsa-miR-148 |
| Heart | hsa-miR-208 |
| Thymus | hsa-miR-96 |
| | hsa-miR-182 |
| Testes | hsa-miR-10b |
| | hsa-let-7e |
| Placenta | hsa-miR-141 |
| | hsa-miR-23a |

We claim:

1. A set of primers specific for a panel of marker genes, wherein the set consists of primer pairs to specifically amplify each of the genes in the panel of marker genes, wherein the panel of marker genes includes the marker genes PRB4, MCSP, ANK1, ESR1, and MMP11 and wherein the set of primers consists of 21 or fewer primer pairs.

2. The set of primers specific for a panel of marker genes of claim 1, optionally including one or more primer pairs to specifically amplify one or more marker genes selected from PRB1, PRB3, HTN3, SEMG1, SEMG2, TGM4, PRM1, PRM2, and MMP7.

3. The set of primers specific for a panel of marker genes of claim 1, wherein the panel of marker genes includes at least one or more additional marker genes for a body fluid sample minimally including saliva, semen, blood, vaginal secretions, and menstrual blood.

4. The set of primers specific for a panel of marker genes of claim 3, wherein the panel of marker genes includes one or more additional marker genes for a body fluid sample selected from saliva, semen, saliva containing mucus, vaginal secretions, blood, and menstrual blood.

5. A set of primers specific for a panel of marker genes, wherein the set consists of primer pairs to specifically amplify each of the genes in the panel of marker genes, wherein the panel of marker genes consists of the marker genes PRB4, MCSP, ANK1, ESR1, and MMP11 and optionally includes one or more primer pairs to specifically amplify one or more marker genes selected from PRB1, PRB3, HTN3, SEMG1, SEMG2, TGM4, PRM1, PRM2, and MMP7.

6. A method for identifying a forensic sample containing nucleic acid comprising:
combining a set of primer pairs to specifically amplify each of the genes in a panel of marker genes, wherein the panel of marker genes includes the marker genes PRB4, MCSP, ANK1, ESR1, and MMP11 with at least some of the nucleic acid from the sample and a polymerase;
amplifying the nucleic acid from the sample with the set of primer pairs, wherein the set of primers consists of 21 or fewer primer pairs;
generating an expression profile for the panel of marker genes; and
identifying the forensic sample.

7. The method of claim 6, optionally including one or more primer pairs to specifically amplify one or more marker genes selected from PRB1, PRB3, HTN3, SEMG1, SEMG2, TGM4, PRM1, PRM2, and MMP7.

8. The method of claim 6, wherein the amplifying comprises a polymerase chain reaction.

9. The method of claim 6, wherein the generating comprises using a reporter probe, a substrate, a nucleic acid dye, a microfluidics device, or combinations thereof.

10. The method of claim 6, wherein the polymerase comprises a DNA-dependent DNA polymerase or an RNA-dependent DNA polymerase and a DNA-dependent DNA polymerase.

11. The method of claim 6, wherein the amplifying comprises a first amplification reaction comprising a multiplicity of different gene-specific primer pairs and a second amplification reaction comprising a single-plex amplification reaction.

12. The method of claim 11, wherein the second amplification reaction comprises a multiplicity of different single-plex amplification reactions performed in parallel.

13. The method of claim 12, wherein the multiplicity of parallel single-plex amplification reactions occur in a microfluidics device.

14. The method of any one of claims 6-13, wherein the forensic sample is a body fluid sample.

15. The method of claim 14, wherein the body fluid sample is selected from blood, semen, saliva, vaginal secretions, and menstrual blood.

16. A kit comprising of a set of primers specific for a panel of marker genes, wherein the set of primers consists of primer pairs to specifically amplify each of the genes in the panel of marker genes, wherein the panel of marker genes includes the marker genes PRB4, MCSP, ANK1, ESR1, and MMP11, wherein the set of primers consists of 21 or fewer primer pairs.

17. The kit of claim 16, optionally including one or more primer pairs to specifically amplify one or more marker genes selected from PRB1, PRB3, HTN3, SEMG1, SEMG2, TGM4, PRM1, PRM2, and MMP7.

18. The kit of claim 16, further comprising one or more of a polymerase; nucleotide triphosphates (NTPs), wherein the NTPs can be ribonucleotide triphosphates (rNTPs) and/or deoxyribonucleotide triphosphates (dNTPs); a reporter probe; a nucleic acid dye; a miRNA linker probe; an internal reference dye; a control sequence or internal standard; or combinations thereof.

19. The kit of claim 16, further including a microarray and/or a microfluidics device.

* * * * *

UNITED STATES PATENT AND TRADEMARK OFFICE
CERTIFICATE OF CORRECTION

PATENT NO. : 8,039,234 B1
APPLICATION NO. : 11/751845
DATED : October 18, 2011
INVENTOR(S) : Rixun N. Fang and Manohar R. Furtado It is certified that error appears in the above-identified patent and that said Letters Patent is hereby corrected as shown below:

At Claim 4, column 21, line 45, delete the number "3" and substitute the number --2--, therefor.

Signed and Sealed this
Fourth Day of September, 2012

David J. Kappos
*Director of the United States Patent and Trademark Office*